US009846218B2

United States Patent
Huber et al.

(10) Patent No.: US 9,846,218 B2
(45) Date of Patent: Dec. 19, 2017

(54) CALBRATION OF A SENSOR ASSEMBLY FOR USE IN MEDICAL POSITION/ORIENTATION TRACKING

(71) Applicant: General Electric Company, Schenectady, NY (US)

(72) Inventors: William Hullinger Huber, Scotia, NY (US); Bahman E. Kashef, Latham, NY (US); Kaustubh Ravindra Nagarkar, Clifton Park, NY (US)

(73) Assignee: General Electric Company, Niskayuna, NY (US)

( * ) Notice: Subject to any disclaimer, the term of this patent is extended or adjusted under 35 U.S.C. 154(b) by 1004 days.

(21) Appl. No.: 13/731,388

(22) Filed: Dec. 31, 2012

(65) Prior Publication Data

US 2014/0188422 A1    Jul. 3, 2014

(51) Int. Cl.
| | |
|---|---|
| *G01R 35/00* | (2006.01) |
| *G06F 17/11* | (2006.01) |
| *A61B 5/06* | (2006.01) |
| *A61B 5/00* | (2006.01) |

(52) U.S. Cl.
CPC ............. *G01R 35/00* (2013.01); *A61B 5/062* (2013.01); *A61B 5/6852* (2013.01); *A61B 2560/0223* (2013.01)

(58) Field of Classification Search
CPC . G01R 35/00; A61B 5/062; A61B 2560/0223; A61B 5/6852; G06F 17/11
USPC .......................................... 702/104; 324/202
See application file for complete search history.

(56) References Cited

U.S. PATENT DOCUMENTS

| | | | |
|---|---|---|---|
| 7,636,595 B2 | 12/2009 | Marquart et al. | |
| 7,702,379 B2 | 4/2010 | Avinash et al. | |
| 7,971,341 B2 | 7/2011 | Dukesherer et al. | |
| 7,987,001 B2 | 7/2011 | Teichman et al. | |
| 8,233,963 B2 | 7/2012 | Hartmann et al. | |
| 2006/0282151 A1* | 12/2006 | Weber ..................... | A61F 2/856 623/1.11 |
| 2008/0121703 A1 | 5/2008 | Li et al. | |
| 2008/0125997 A1 | 5/2008 | Li et al. | |
| 2010/0137705 A1 | 6/2010 | Jensen et al. | |
| 2010/0305427 A1* | 12/2010 | Huber ................ | A61B 19/5244 600/424 |

(Continued)

FOREIGN PATENT DOCUMENTS

GB    WO 2012146930 A2 *   11/2012   ............. G01N 33/20

OTHER PUBLICATIONS

Wu, Xiaohui "A Direction Space Interpolation Technique for Calibration of Electromagnetic Surgical Navigation Systems", Medical Image Computing and Computer-Assisted Intervention—MICCAI 2003, 2003, pp. 215-222, vol. 2879/2003.*

(Continued)

*Primary Examiner* — Yoshihisa Ishizuka
(74) *Attorney, Agent, or Firm* — Nitin N. Joshi

(57) ABSTRACT

A position and orientation system and method is provided. A magnetoresistance sensor is provided having a sensor array configured to measure magnetic fields and a metallic coil positioned within the magnetoresistance sensor. In certain embodiments, the magnetic coil may be used to generate a known magnetic field that, when measured by the sensor array, may be used to determine or update a calibration constant for the system.

19 Claims, 4 Drawing Sheets

(56) References Cited

U.S. PATENT DOCUMENTS

2011/0201923 A1    8/2011  Shen et al.
2013/0135439 A1*  5/2013  Kakuko ................. H04N 13/00
                                                                      348/46

OTHER PUBLICATIONS

Xiaohui et al., "A Direction Space Interpolation Technique for Calibration of Electromagnetic Surgical Navigation Systems", Medical Image Computing and Computer-Assisted Intervention—MICCAI 2003, 2003, pp. 215-222, vol. 2879/2003.
U.S. Appl. No. 13/538,573, filed Jun. 29, 2012, Kaustubh Ravindra Nagarkar.
U.S. Appl. No. 13/538,595, filed Jun. 29, 2012, Kaustubh Ravindra Nagarkar.
U.S. Appl. No. 13/728,831, filed Dec. 27, 2012, Andriy Yaroshenko.

* cited by examiner

CALBRATION OF A SENSOR ASSEMBLY FOR USE IN MEDICAL POSITION/ORIENTATION TRACKING

BACKGROUND

The subject matter disclosed herein relates generally to sensors that may be used to provide position/orientation information for an instrument, implant or device used in a medical context, such as in a surgical or interventional context. In particular, the subject matter relates to calibrating a sensor assembly to improve the accuracy and precision of the position/orientation information.

In various medical contexts it may be desirable to acquire position and/or orientation information for a medical instrument, implant, or device that is navigated or positioned (externally or internally) relative to a patient. For example, in surgical and/or interventional contexts, it may be useful to acquire position and/or orientation information for a medical device, or portion of a medical device, even when the device or relevant portion is otherwise out of view, such as within a patient's body. Likewise, in certain procedures where an imaging technique is used to observe all or part of the position and orientation information, it may be useful to have position and orientation information derived from the tracked device itself that can be related to other data, such as image data that may be contemporaneously acquired. In such medical contexts, electromagnetic (EM) sensors may be implemented to provide the position/orientation information for the medical instrument, implant, or device.

It may be desirable to calibrate the EM sensors before use in a surgical or interventional context, so that position/orientation information may be obtained with a high level of precision and accuracy. Unfortunately, for medical applications that last several minutes to a few hours, an initial calibration of the EM sensor may not sufficiently reduce position/orientation errors originating at the EM sensor over the entire course of the procedure. Accordingly, it may be desirable to calibrate EM sensors as they are operating in surgical or interventional applications so that a high level of precision and accuracy can be maintained while position/orientation information is obtained for the medical device. While it may be desirable to calibrate EM sensors at the location of use, in practice it may be difficult to provide for portable calibration methods that do not need large calibration equipment. Furthermore, it may be difficult to provide fast, high-throughput calibration for EM sensors as they are being used to acquire position/orientation information during surgical or interventional procedures, such as, for example, when the EM sensors are used within a patient's body.

BRIEF DESCRIPTION

In one embodiment, a position and orientation system is provided having a magnetoresistance sensor with a sensor array configured to measure magnetic fields and a metallic coil positioned within the magnetoresistance sensor at a fixed distance from the sensor array. The system also provides a controller configured to at least read out data from the sensor array. The system also includes processing circuitry coupled to the controller. The processing circuitry processes data read out from the sensor array in response to a calibration magnetic field generated by the metallic coil to calculate and update a calibration constant. The processing circuitry also processes data read out from the sensor array in response to an external magnetic field using the calibration constant to generate position and orientation data for a surgical or interventional device.

In another embodiment, a method is provided comprising driving a transmitter coil to generate a navigational electromagnetic field, and measuring a calibration electromagnetic field generated by a calibration coil at a calibration frequency not in use by the transmitter coil by detecting the calibration electromagnetic field with a sensor array on an electromagnetic sensor. The method also includes calculating or updating a calibration constant based on the measured calibration electromagnetic field using processing circuitry, and calibrating the electromagnetic sensor at one or more transmitter frequencies based on the calibration constant. The method also includes measuring the navigational electromagnetic field using the calibrated sensor array on the electromagnetic sensor, and generating position and orientation data for a surgical or interventional device based on the measured navigational electromagnetic field and the calibration constant.

In another embodiment, one or more tangible, non-transitory, machine-readable media collectively storing instructions executable by a processor is provided. The one or more tangible, non-transitory, machines readable media may drive a transmitter coil to generate a navigational electromagnetic field, measure a calibration electromagnetic field generated by a calibration coil at a calibration frequency not in use by the transmitter coil by detecting the calibration electromagnetic field with a sensor array on an electromagnetic sensor, calculate or update a calibration constant based on the measured calibration electromagnetic field using processing circuitry, calibrate the electromagnetic sensor at one or more transmitter frequencies based on the calibration constant, measure the navigational electromagnetic field using the calibrated sensor array on the electromagnetic sensor, and generate position and orientation data for a surgical or interventional device based on the measured navigational electromagnetic field and the calibration constant.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
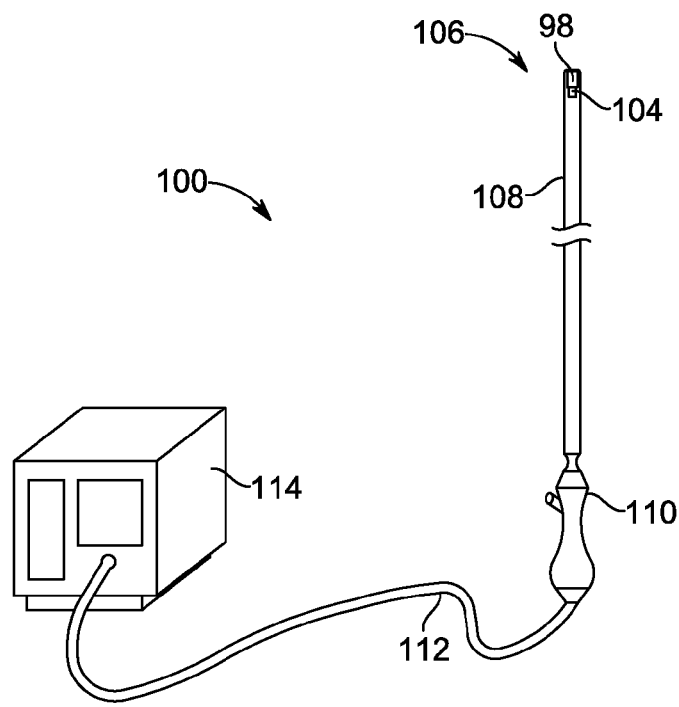
FIG. 1 depicts an example of an interventional device suitable for use with one or more of the position/orientation system.

One or more specific embodiments of the present disclosure will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements.

As discussed herein, components of a position/orientation system may generally be attached to various types of surgical or interventional instruments, implants, devices, or any other suitable device for which position and orientation information may be desired during surgical or interventional contexts. The position/orientation system is suitable for correcting and tracking the position and orientation of the various surgical or interventional devices. In particular, in certain embodiments disclosed herein, the position/orientation system includes one or more electromagnetic (EM) sensors that measure or respond to an external magnetic field and which may be used to determine spatial properties, such as position coordinates and/or orientation information. In certain embodiments, the EM sensor may be a one one-axis or two-axis magnetoresistance sensor configured to generate position and orientation information in the presence of an externally applied magnetic field. Such sensors may become desensitized over time with exposure to variations in temperatures, magnetic fields, or other variables present in the sensor environment. As a result, the sensors may provide errors in generating the position and/or orientation information while operating in environments with unpredictable variations in temperatures, magnetic fields, and the like. Accordingly, it may be desirable to provide fast and portable methods of sensor calibration at the location of use.

In some embodiments, the magnetoresistance sensor may have at least one metallic coil that may be used for dynamic calibration operations, referred to herein as a calibration coil. In particular, the calibration coil is configured to generate known magnetic field at a specified frequency, which may then be extrapolated to calibrate the sensor at other frequencies. In certain embodiments, a calibration system provides an initial calibration prior to operating the sensor, or a single calibration at the location where the sensor is in operation. In other embodiments, the calibration system may function as part of a feedback loop used to calibrate the sensor during use, continuously or intermittently. In such embodiments, a calibration constant may be generated or updated based on information derived using a calibration coil to continuously calibrate the sensor while it is in use. In such an embodiment, the calibration system may allow for portable calibration (e.g., calibration without fixed calibration equipment) at the site of the sensor's operation, such as in an operating room or at the site of an interventional or surgical procedure.

In certain embodiments, calibrating the sensor continuously during navigation may account for variations in temperatures, magnetic fields, or other factors that affect the sensor output during sensor operation (i.e., device navigation). The navigation process involves detecting the magnetic field transmitted by transmission coils (e.g., twelve transmission coils) at various frequencies and generating position and orientation information based on the detected magnetic field. In addition, a calibration may be performed continuously or periodically to address the factors noted above. In particular, a separate calibration coil may be provided, such as at a fixed distance from the sensing components, that is capable of generating a known magnetic field that can be sensed by the sensing components and used to derive, and update, a calibration constant ($\Gamma$) that can be used to correct or otherwise adjust the measured position and orientation information derived using the transmission coils. For example, in one embodiment, the calibration process involves continuously calculating the calibration constant so that it may be used to continuously calibrate the sensor during navigation of the device. The calibration process accounts for variations in temperatures, magnetic fields, or other factors that may affect the sensor output similarly at any frequency. As such, the impact on the sensor calibration can be compensated at all frequencies by simply tracking one frequency with the calibration coil. Furthermore, the calibration process may be based on the assumption that the calibration coil is positioned at a fixed location within the sensor. Therefore, the relationship between the magnetic field and the current (e.g., B/I value) is constant, and does not change with variations in temperatures, magnetic fields, or other environmental factors that may affect the sensor output.

With the foregoing in mind, and turning to FIG. 1, an example of a medical device 100 is depicted that is suitable for use with a position/orientation assembly 98 having an electromagnetic (EM) sensor 104. In this example, the medical device 100 is a catheter suitable for insertion into and navigation through the vasculature of a patient. Though a catheter is provided by way of example, the position/orientation assembly 98 discussed herein may be provided on or in various other types of surgical or interventional instruments, implants or devices. Examples of such instruments, implants or devices include, but are not limited to: implant, probe, awl, drill, aspirator, forceps, blade, screw, nail, pin, k-wire, needle, cannula, introducer, catheter, guidewire, stent, heart valve, filter, endoscope, laparoscope, or electrode, endoscopes or other intrabody camera devices, or any other suitable device for which position and orientation information may be desired during surgical or interventional use.

The depicted medical device 100 (e.g., catheter) includes a distal end or tip 106 in which a position/orientation assembly 98 (e.g., an EM sensor 104, substrate on which the sensor 104 is disposed, potting materials, and so forth) may be positioned. A shaft 108 is in communication with the tip 106, and the shaft 108 connects the tip 106 with a handle assembly 110 that may be used to manipulate and operate the medical device 100 (e.g., catheter). In certain instances, the handle assembly 110 may communicate, such as via cable 112, with an operator console 114 that allows a user to control certain aspects of the catheter function and operation. While a single position/orientation assembly 98 positioned in the distal end or tip 106 is shown by way of example, in other embodiments, two, three, four or more position/orientation assemblies 98 may be provided in the medical device. In other embodiments, each position/orientation assembly 98 may include one, two, three, four, or more EM sensors 104 configured to obtain position/orientation information for the medical device 100.

In a general sense, the EM sensor 104 may be implemented as an EM receiver and/or EM transmitter, i.e., as EM components that transmit and/or receive using portions of the EM spectrum, such as the radiofrequency (RF) portion of the electromagnetic spectrum. Any one or a combination of the EM sensors 104 may be used as transmitting or receiving coils. The signals sensed by EM sensor 104 that are fixed in relation to the medical device 100 may be used to determine the spatial properties of the medical device 100, for example, the position (e.g., the X-, Y-, and Z-coordinates) and orientation (e.g., the pitch, yaw, and roll angles).

Figure 6:
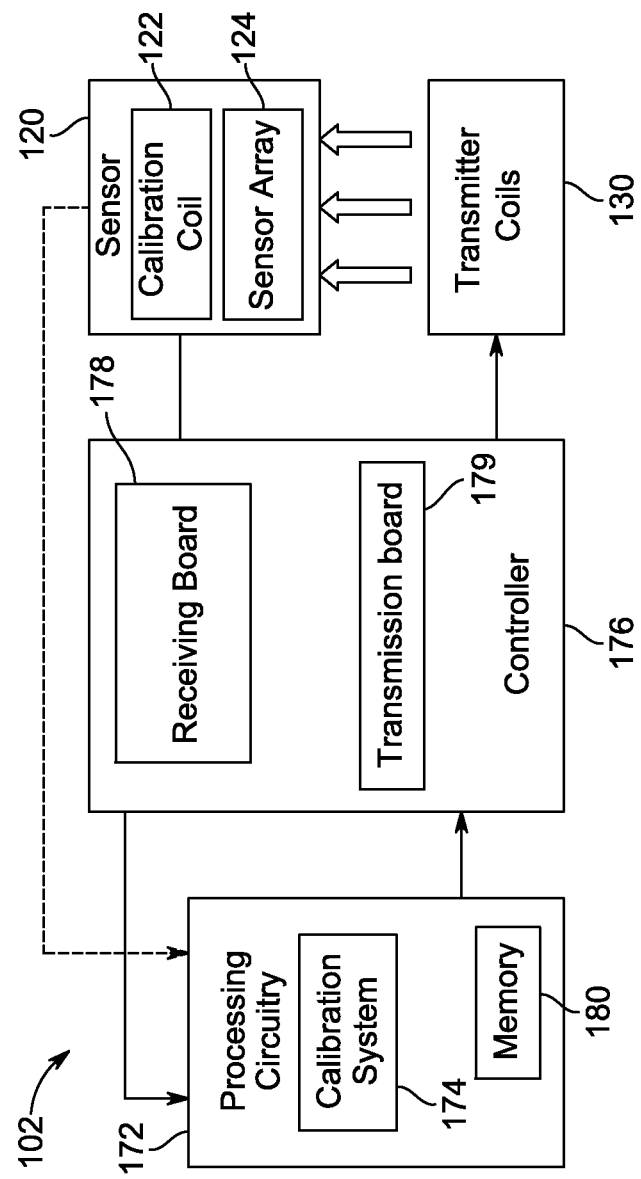
FIG. 6 is a schematic diagram of an embodiment of a navigation system having a position/orientation system and a calibration system, in accordance with aspects of the present disclosure.

In accordance with an embodiment, the EM sensor 104 generates spatial information related to the medical device 100, such as position coordinates or orientation information. That is, a position/orientation system 102 (as depicted in FIG. 6) processes signals acquired from the EM sensors 104 in the medical device 100 to generate position/orientation information related to the medical device 100. The position/orientation system 102 further includes processing circuitry 172 (as described in FIG. 6) and/or a memory 180 for subsequent processing of position/orientation signals from the EM sensor 104, as discussed in further detail below in FIG. 3. In some embodiments, the EM sensor 104 is a two-axis magnetoresistance sensor 120 configured to generate position and orientation information in the presence of an externally applied magnetic field. In other embodiments, the EM sensor 104 may be a one-axis magnetoresistance sensor or may sense along 3 or more axes. The magnetoresistance sensor 120 may be affected by variations in temperature, magnetic field, or other field variables within the environment of the medical device 100. Accordingly, it may be desirable to calibrate the magnetoresistance sensor 120 to reduce errors in position and/or orientation resulting from unpredictable variations in the sensor field relating to temperature, magnetic field, and the like.

Figure 2:
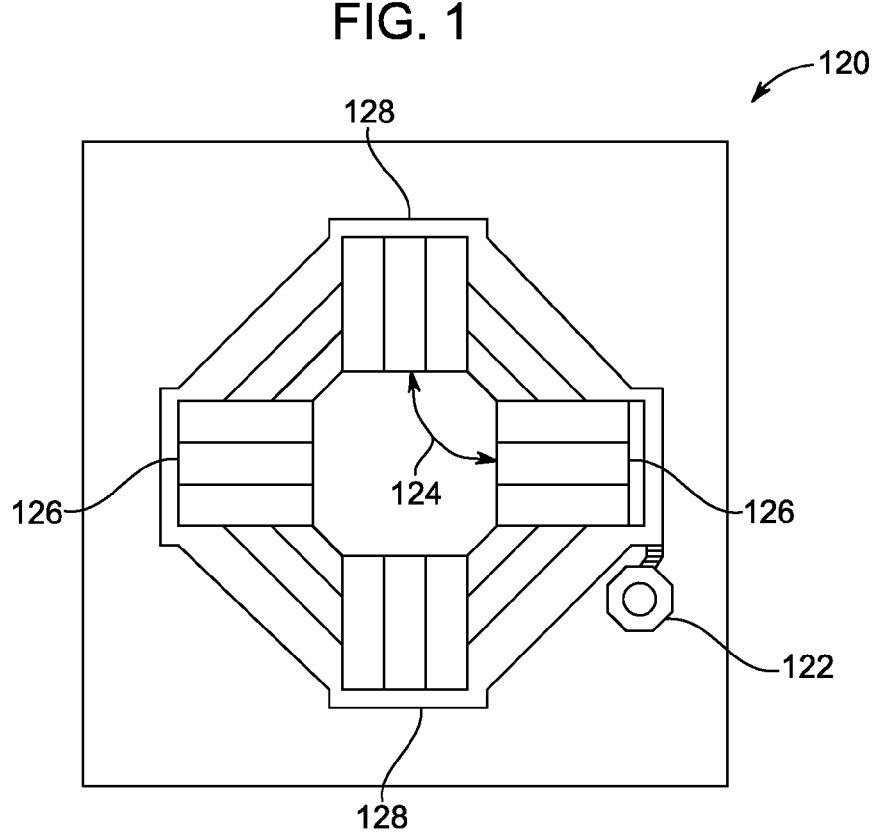
FIG. 2 depicts a position/orientation sensor with a calibration coil, in accordance with aspects of the present disclosure.

Turning to FIG. 2, an enlarged top view of an exemplary embodiment of the magnetoresistive sensor 120 having a calibration coil 122 is provided in accordance with aspects of the present disclosure. The magnetoresistive sensor 120 generates signals indicative of a change in electrical resistance of a conductor or semiconductor when a magnetic field is applied and the magnetoresistive sensor 120 moves or changes orientation with respect to the externally applied magnetic field. That is, in such sensors, the device's resistance at various sensing elements depends upon the magnetic field applied.

In certain embodiments, the magnetoresistance sensor 120 includes a magnetometer or magnetoresistive sensor arrangement, such as an integrated two-axis sensor array 124 suitable for providing position and/or orientation information in the presence of an external magnetic field. In other embodiments, the magnetoresistance sensor 120 may be configured as a one-axis sensor or may be configured as a three or more axis sensor array. In one implementation, the position and orientation sensor array 124 is a solid-state (i.e., silicon based) device having a respective magnetic sensor for each of two perpendicular axes (i.e., such as a first axial element 126 which may be a miniature surface mount sensor, and a second axial element 128 which may be another miniature surface mount sensor perpendicular to the first). In combination, the two axial elements of the sensor array 124 are sufficiently sensitive to generate position (i.e., x, y, and z position data) and orientation data (i.e., roll, pitch, and yaw orientation data) in the presence of a magnetic field. In certain implementations, the position and orientation sensor array 124 operates at a low voltage (e.g., 2.0 V or less) and over a wide magnetic field range (e.g., ±10 Oe). Further, in certain implementations the position and orientation sensor array 124 has a very low noise floor at metal tolerant frequencies (e.g., 10-1000 times lower than microcoils) and has a compact form factor (e.g., as small as about 0.4 mm in width). In practice, the position and orientation sensor array 124 may be a multi-layer design, such as having layers corresponding to an offset strap (e.g., calibration coil 122) used to calibrate the sensor array 124, a set-reset strap allowing the respective magnetic sensors of the array 124 to be reset, and a resistor bridge used to measure the magnetic field.

In certain embodiments, the bridge resistance of the resistor bridge (which may measure the strength of the external magnetic field) in the magnetoresistive sensor 120 may depend linearly on the temperature of the environment. Indeed, with large variations in external temperature, the strength of the magnetoresistive effect may decrease. Furthermore, the bridge may not be able to fully compensate for the temperature dependence of the resistor bridge internally. As such, the sensitivity of the magnetoresistive sensor 120 (e.g., defined as the slope of the output voltage versus external magnetic field) may be affected, and may limit the magnetoresistive sensor 120 from measuring the magnetic field with precision and accuracy in an environment with high temperatures or variations in temperatures.

With this in mind, in one implementation, the calibration coil 122 is configured or designed to calibrate the magnetoresistive sensor 120 to reduce the errors in position and/or orientation resulting from unpredictable variations in the magnetoresistive sensor 120 environment relating to temperature, magnetic field, and the like. In some embodiments, the calibration coil 122 calibrates the magnetoresistive sensor 120 based on the structural design of the calibration coil 122 in relation to the sensor array 124. In particular, the calibration coil 122 may be at a fixed position in relation to the two magnetic sensors (i.e., respective first and second axial elements 126, 128) of the sensor array 124, as depicted in FIG. 2. As such, the external magnetic field relative to the electrical resistance generated (e.g., B/I value) of the calibration coil 122 is always constant. Indeed, the B/I value of the calibration coil 122 may be a constant value that is known at the time of manufacturing the magnetoresistive sensor 120. Furthermore, the B/I value is a geometric quantity that is independent of the excitation current (e.g., which may create the electrical resistance) generated by the magnetoresistive sensor 120. It may be useful to use the B/I value in an algorithm for calibrating the magnetoresistive sensor 120 because the B/I value of the calibration coil 122 generally does not change with temperature, magnetic field, or similar variations in the magnetoresistive sensor 120 environment.

Accordingly, the B/I value of the calibration coil 122 may be used to derive a calibration algorithm that determines a calibration constant (e.g., sensor-to-magnetic field transformation constant) for the calibration coil 122 at a specified frequency for each sensor of the sensor array 124 (e.g., axial elements 126 and 128). Furthermore, the calibration algorithm may be used to determine a transformation constant (e.g., sensor-to-magnetic field transformation constant) at a specified frequency for a set of transmitter coils 130 (as depicted in FIG. 6 below) as they are received at the first and second axial elements 126, 128 of the sensor array 124. In certain embodiments, the transmitter coils 130 may be components of the position/orientation system 102 that are used to generate the external magnetic field or which may be used to generate a reference calibration field distinct from the external magnetic field used in position and orientation sensing. As discussed herein, the position/orientation system 102 may have twelve transmitter coils. In other embodiments, a number of transmitter coils or than twelve may be employed. The calibration constants for the calibration coil 122 may be used to normalize the transformation constants for each of the transmitter coils 130 (e.g., each of the twelve transmitter coils), and may calibrate the magnetoresistive sensor 120 at other frequencies. The calibration process is outlined in greater detail in FIG. 3 below.

Figure 3:
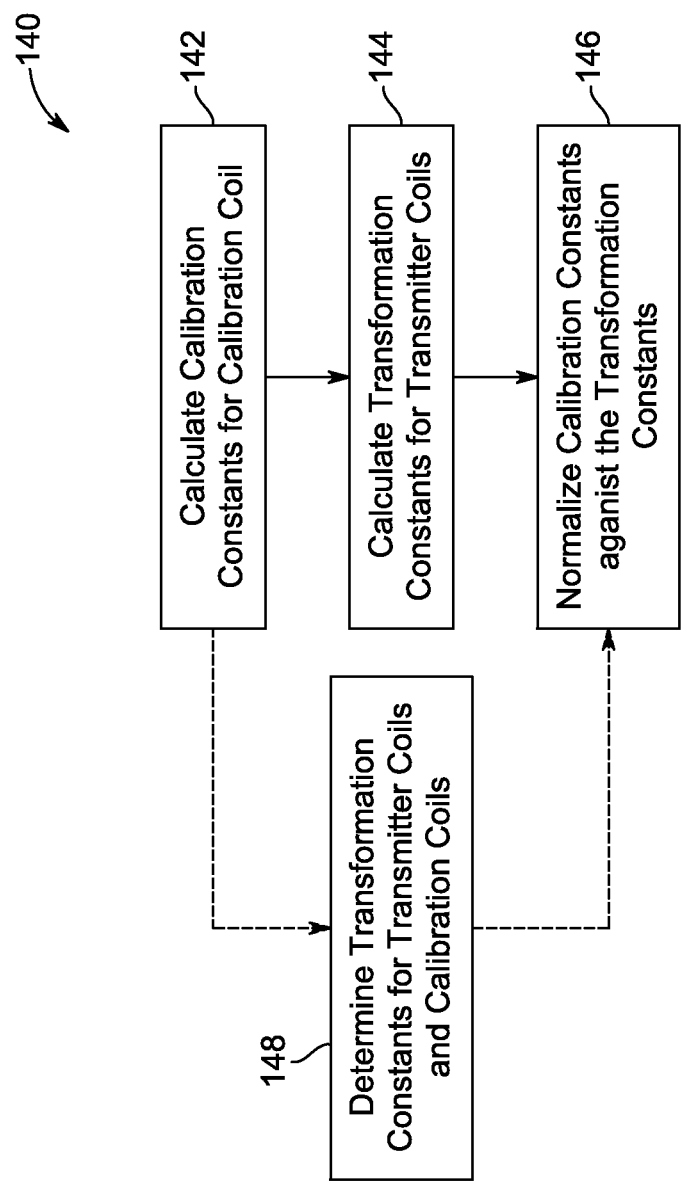
FIG. 3 is a flowchart chart depicting an embodiment of a method for calibrating the sensor based on a calibration algorithm, in accordance with aspects of the present disclosure.

FIG. 3 is a flowchart depicting an embodiment of a method 140 for calibrating the magnetoresistive sensor 120 based on a calibration algorithm. As generally noted above, the calibration system 174 (described below in FIG. 6) uses a calibration algorithm to calibrate the magnetoresistive sensor 120, where the calibration algorithm takes into account variations in temperatures, magnetic fields, or other factors that affect the magnetoresistive sensor 120 output similarly at any frequency. As such, the effects of these variations on the magnetoresistive sensor 120 can be compensated at all frequencies by simply tracking one frequency with the calibration coil 122 (as further described in FIG. 4). In certain embodiments, the response of the calibration coil 122 is determined at the first and second axial elements 126 and 128 when the calibration coil 122 is driven at a frequency of approximately about 1 kHz. Using the specified frequency (e.g., 1 kHz), sensor-to-magnetic field transformation constants (e.g., calibration constants) are determined for the calibration coil 122 at both the axial elements 126 and 128. Similarly, the calibration algorithm may be used to determine sensor-to-magnetic field transformation constants for the transmitter coils 130 (e.g., transformation constants), as they are sensed by the first and second axial elements 126 and 128. In certain embodiments, there may be twelve transmitter coils 130, while in other embodiments, there may be any number of transmitter coils 130. The transformation constants determined for the transmitter coils 130 may be normalized against the calibration constants determined for the calibration coil 122. As such, an output of calibration coil 122 at a specified frequency (e.g., 1 kHz) may be used to calibrate the magnetoresistive sensor 120 at other frequencies.

As depicted in block 142, a sensor-to-magnetic field transformation constant (e.g., calibration constant, $\Gamma_A$ or $\Gamma_B$) is calculated for the calibration coil 122 as received by the sensor array 124. In particular, the calibration coil 122 is at a fixed distance from the sensor array 124. More specifically, $\Gamma_A$ may be calculated for the calibration coil 122 at the first axial element 126 at a specified frequency, and $\Gamma_B$ may be calculated for the calibration coil 122 at the second axial element 128 at the specified frequency. In certain embodiments, the calibration coil 122 is tracked at a frequency of about 1 kHz. A calibration algorithm may be used to determine the calibration constants $\Gamma_A$ or $\Gamma_B$ for the calibration coil 122 at the specified frequency, as described with respect to equations (1) through (4) below.

With the forgoing in mind, the measured voltage response from the first and second axial elements 126 and 128 of the sensor array 124 can be described in equation (1) as:

$$\begin{pmatrix} V_A \\ V_B \end{pmatrix} = \frac{1}{G_{RX}} \begin{pmatrix} v_A \\ v_B \end{pmatrix} \quad (1)$$

where $v_A$ is the measured voltage response from the first axial element 126 of the sensor array 124, $v_B$ is the measured voltage response from the second axial element 128 of the sensor array 124, and $G_{RX}$ is the gain of the pre-amplifier of the magnetoresistive sensor 120. In addition, the $I_{TX}$ of the magnetoresistive sensor 120 can be described in equation (2) as:

$$I_{TX} = \frac{i_{TX}}{G_{TX} \cdot R_{TX}} \quad (2)$$

where $i_{TX}$ is the measured transmitter current, $R_{TX}$ is the sensor resistor of the current measuring circuit, and $G_{TX}$ is the gain of the pre-amplifier of the current measuring circuit. Furthermore, the change in the measured voltage response from the first and second axial elements 126 and 128 of the sensor array 124 can be described in equation (3) as:

$$\begin{pmatrix} \delta V_A \\ \delta V_B \end{pmatrix} = \frac{1}{V_{BRDG}} \begin{pmatrix} V_A \\ V_B \end{pmatrix} \quad (3)$$

where $V_{BRDG}$ is the bridge bias, $v_A$ is the measured voltage response from the first axial element 126 of the sensor array 124, and $v_B$ is the measured voltage response from the second axial element 128 of the sensor array 124. Finally, calibration constants $\Gamma_A$ or $\Gamma_B$ may be calculated for the calibration coil 122 at a specified frequency for the first and second axial elements 126 and 128 of the sensor array 124, and may be described in equation (4) as:

$$\begin{pmatrix} \Gamma_A \\ \Gamma_B \end{pmatrix} = \frac{1}{KI_{TX}} \begin{pmatrix} \delta V_A \\ \delta V_B \end{pmatrix} \quad (4)$$

where K is the B/I value of the coil, $I_{TX}$ may be calculated from equation (2), and the change in the measured voltage response from the first and second axial elements 126 and 128 of the sensor array 124 may be calculated from equation (4). Using the calibration algorithm, as described above, a sensor-to-magnetic field transformation constant (e.g., calibration constants, $\Gamma_A$ or $\Gamma_B$) may be calculated for the calibration coil 122.

As depicted in block 144, a sensor-to-magnetic field transformation constant (e.g., transformation constants) may be calculated for transmitter coils 130, as they are received by the first and second axial elements 126 and 128 in the sensor array 124. In particular, the calibration algorithm, as derived in block 142, may be used to generate the transformation constants. As such, in certain embodiments, twelve transformation constants are generated at the first axial element 126 (e.g., $\Gamma_{A1 \ldots A12}$), and twelve transformation constants are generated at the second axial element 128 (e.g., $\Gamma_{B1 \ldots B12}$). In other embodiments, any number of transformation constants may be measured.

In certain embodiments, as depicted in block 146, the calibration constants for the calibration coil 122 may be used to normalize the transformation constants for the twelve transmitter coils 130. Furthermore, the calibration coil 122 may be used to calibrate the magnetoresistive sensor 120 at other frequencies after the signal response for the calibration coil 122 is measured at the first and second axial elements 126 and 128 in the sensor array 124. More specifically, calibration constants $\Gamma_A$, calculated for the calibration coil 122 with respect to the first axial element 126, may be used to normalize the transformation constants $\Gamma_{A1\ldots A12}$ calculated for the twelve transmission coils 130. Indeed, the calibration constants $\Gamma_A$, calculated for the calibration coil 122 with respect to the first axial element 126, may also be used to calibrate the entire system, which may include calibrating the calibration coil 122, as described in equations (5) and (6):

$$\Gamma_A = \begin{pmatrix} \Gamma_{A1} \\ \Gamma_{A2} \\ \Gamma_{A3} \\ \vdots \\ \Gamma_{A12} \end{pmatrix} \quad (5)$$

$$|\Gamma_A| = \frac{1}{\Gamma_{A1}} \begin{pmatrix} \Gamma_{A1} \\ \Gamma_{A2} \\ \Gamma_{A3} \\ \vdots \\ \Gamma_{A12} \end{pmatrix} = \begin{pmatrix} 1 \\ \Gamma_{A2}/\Gamma_{A1} \\ \Gamma_{A3}/\Gamma_{A1} \\ \vdots \\ \Gamma_{A12}/\Gamma_{A1} \end{pmatrix} \quad (6)$$

where $\Gamma_A$ is the calibration constant calculated for the calibration coil 122 at the first axial element 126, and $\Gamma_{A1\ldots A12}$ are the transformation constants calculated for the transmission coils 130 at the first axial element 126. Likewise, calibration constant $\Gamma_B$, calculated for the calibration coil 122 at the second axial element 128, may be used to normalize the transformation constants $\Gamma_{B1\ldots B12}$ calculated for the transmission coils 130 at the second axial element 128, as described in equations (7) and (8):

$$\Gamma_B = \begin{pmatrix} \Gamma_{B1} \\ \Gamma_{B2} \\ \Gamma_{B3} \\ \vdots \\ \Gamma_{B12} \end{pmatrix} \quad (7)$$

$$|\Gamma_B| = \frac{1}{\Gamma_{B1}} \begin{pmatrix} \Gamma_{B1} \\ \Gamma_{B2} \\ \Gamma_{B3} \\ \vdots \\ \Gamma_{B12} \end{pmatrix} = \begin{pmatrix} 1 \\ \Gamma_{B2}/\Gamma_{B1} \\ \Gamma_{B3}/\Gamma_{B1} \\ \vdots \\ \Gamma_{B12}/\Gamma_{B1} \end{pmatrix} \quad (8)$$

where $\Gamma_B$ is the calibration constant calculated for the calibration coil 122 at the second axial element 128, and $\Gamma_{B1\ldots B12}$ are the transformation constants calculated for the transmission coils 130 at the second axial element 128.

In certain embodiments, during normal tracking of the medical device 100, only the calibration constants $\Gamma_A$ or $\Gamma_B$ are periodically calculated. As depicted in block 148, once these values are known, the transformation constants for the transmitter coils 130 may be determined using, for example, equations (9) and (10):

$$\Gamma_A = \Gamma_{A1} \cdot |\Gamma_A| \quad (9)$$

$$\Gamma_B = \Gamma_{B1} \cdot |\Gamma_B| \quad (10)$$

In particular, equation (9) may be repeated by replacing $\Gamma_{A1}$ with $\Gamma_{A2\ldots A12}$, such that transformation constants for each of the transmitter coils are calculated at the first axial element 126 of the sensor array 124. Similarly, equation (10) may be repeated by replacing $\Gamma_{B1}$ with $\Gamma_{B2\ldots B12}$, such that transformation constants for each of the transmitter coils 130 and the calibration coil 122 are calculated at the second axial element 128 of the sensor array 124.

In this manner, for a particular frequency at the first and second axial elements 126 and 128 of the sensor array 124, the magnetoresistive sensor 120 may be calibrated by implementing the calibration algorithm. In particular, the calibration algorithm may be used to calculate calibration constants for the calibration coil 122 and to calculate transformation constants for the transmitter coils 130 and the calibration coil 122. Finally, the magnetoresistive sensor 120 may be calibrated at other frequencies when the calibration constants of the calibration coil 122 calculated from the specified frequency are used to normalize the transformation constants of the transmitter coils 130 at all other frequencies. In certain embodiments, the calibration coil is tracked at a frequency of approximately about 1 kHz.

Figure 4:
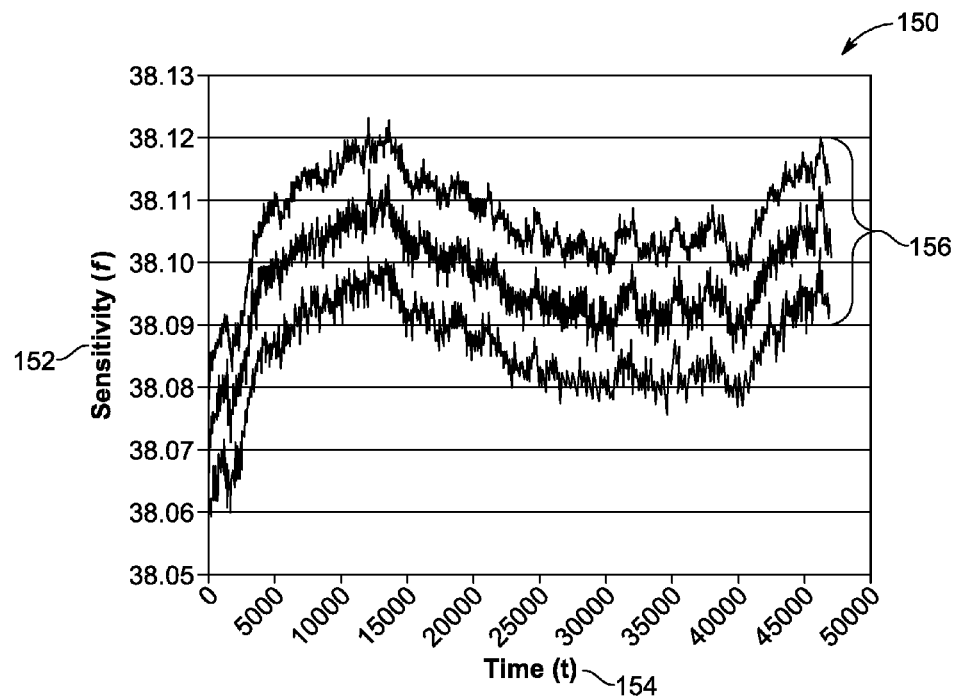
FIG. 4 is an example of a graphical diagram depicting the effect of environmental variations on the sensitivity of the sensor over time, in accordance with aspects of the present disclosure.

FIG. 4 is an example of a graphical diagram 150 depicting the effect of external variations in temperature on the sensitivity of the magnetoresistive sensor 120. As described above in FIG. 2, with large variations in external temperature, the strength of the magnetoresistive effect may decrease, and the sensitivity of the magnetoresistive sensor 120 (e.g., defined as the slope of the output voltage versus external magnetic field) may be affected. As such, the magnetoresistive sensor 120 may be limited from measuring the magnetic field with precision and accuracy in an environment with high temperatures or variations in temperatures. The long term effects of such environmental factors on the magnetoresistive sensor 120 may be a degradation of sensor properties, or even an output signal that varies independently of the measured sensor properties (i.e., magnetic field). These effects, also known as drift, are depicted in FIG. 4.

As illustrated in FIG. 4, the sensitivity 152 of the magnetoresistive sensor 120 over time 154 is depicted over various frequencies 156 (e.g., between approximately 15 Hz and 14 kHz). In the illustrated embodiment, the magnetoresistive sensor 120 displays drift over time 154 that is linearly proportional for each frequency measured. In other words, the effect of external variations in temperature on the sensitivity of the magnetoresistive sensor 120 over time 154 is proportionally the same across a wide range of frequencies 156. However, it may not be desirable to use sensors 120 that exhibit drift because the magnetoresistive sensor 120 may be imprecise or inaccurate in measuring external magnetic fields. As such, sensors 120 that exhibit drift may lead to reduce position/orientation errors originating at the EM sensor while it is in use.

Figure 5:
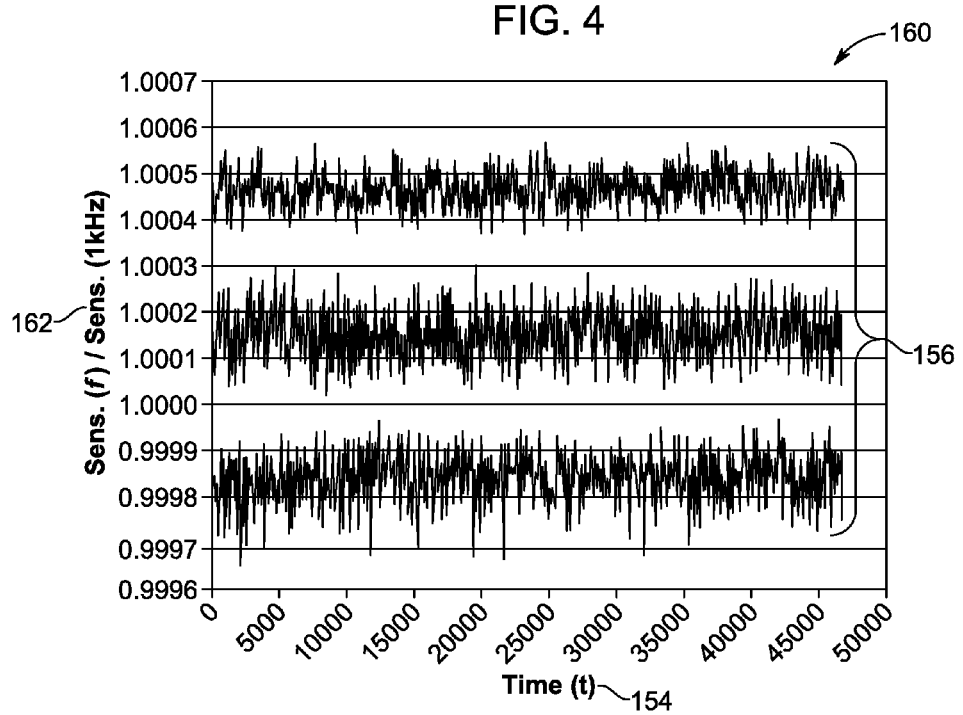
FIG. 5 is an example of a graphical diagram depicting the effect of calibrating the sensor on the sensitivity of the sensor over time, in accordance with aspects of the present disclosure.

FIG. 5 is an example of a graphical diagram 160 depicting the effect of calibrating the magnetoresistive sensor 120 on the sensitivity of the magnetoresistive sensor 120 over time 154 (e.g., while in use). As described above in FIG. 3, a calibration algorithm may be implemented to calibrate the magnetoresistive sensor 120 in an ongoing manner As such, the effects of these variations on the magnetoresistive sensor 120 can be compensated at all frequencies by simply tracking one frequency with the calibration coil 122. For example, an output of the calibration coil 122 at a specified frequency (e.g., 1 kHz) may be used to calibrate the magnetoresistive sensor 120 at any other frequency. In certain embodiments, sensor-to-magnetic field transformation constants may be determined to aid in transforming the specified frequency outputs into a means for calibrating the magnetoresistive sensor 120.

Keeping the foregoing in mind, FIG. 5 illustrates the sensitivity 162 of the magnetoresistive sensor 120 over time 154 after it has been normalized with the sensor-to-magnetic field transformation constants. In particular, the magnetoresistive sensor 120 does not display drift over time 154. In other words, the effect of external variations in temperature on the sensitivity of the magnetoresistive sensor 120 over time 154 is compensated for across a wide range of frequencies 156. In particular, in the illustrated embodiment 160, the magnetoresistive sensor 120 does not exhibit drift, and as such, the magnetoresistive sensor 120 may reduce the number of position/orientation errors originating at the EM sensor while in use.

FIG. 6 is a schematic diagram of an embodiment of a position/orientation system 102 having processing circuitry 172, a calibration system 174, a controller 176, a magnetoresistive sensor 120 with a calibration coil 122, and transmitter coils 130. The processing circuitry 172 may be adapted to control features enabled by the controller 176, e.g., scanning operations, position/orientation data acquisition, and transmission operations. In particular embodiments, the controller 176 may further include a receiving board 178 and a transmission board 179. The controller 176 may be configured to acquire position/orientation data from one or more sensors 120 at a receiving board 178. In other embodiments, the one or more sensors 120 may provide position/orientation data directly to the processing circuitry.

The processing circuitry 172 is typically coupled to the controller 176. The data collected by the controller 176 may be transmitted to the processing circuitry 172 for subsequent mapping of the EM sensor data, or for subsequent correction of position and/or orientation errors caused by variations in temperature or magnetic fields within the environment of the magnetoresistive sensor 120. The controller 176 may also drive the transmitter coils 130 at particular frequencies in order to generate an external magnetic field. The sensor array 124 of the magnetoresistive sensor 120 may detect the external magnetic field in order to generate position and/or orientation data. In particular, the processing circuitry 172 may include a calibration system 174 for correcting position and orientation errors due to drift in magnetoresistive sensors 120. The processing circuitry 172 may include (or may communicate with) a memory 180 that stores data processed by the processing circuitry 172 or data to be processed by the processing circuitry 172. It should be understood that any type of computer accessible memory device capable of storing the desired amount of data and/or code may be utilized. Moreover, the memory 180 may include one or more memory devices, such as magnetic, solid state, or optical devices, of similar or different types, which may be local and/or remote to the system 102. The memory 180 may store data, processing parameters, and/or computer programs having one or more routines for performing the processes described herein.

As described above in FIG. 2, magnetoresistive sensor 120 includes a magnetometer or magnetoresistive sensor arrangement, such as an integrated two-axis sensor array 124 suitable for providing position and/or orientation information in the presence of an external magnetic field. In other embodiments, the magnetoresistance sensor 120 may be configured for sensing along one-axis or along three or more axes. In one implementation, the position and orientation sensor array 124 is a solid-state (i.e., silicon based) device having a respective magnetic sensor for each of two perpendicular axes (i.e., such as a first axial element 126 which may be a miniature surface mount sensor, and a second axial element 128 which may be another miniature surface mount sensor). In combination, the two magnetic sensors of the sensor array 124 are sufficiently sensitive to generate position (i.e., x, y, and z position data) and orientation data (i.e., roll, pitch, and yaw orientation data) in the presence of a magnetic field. This information, along with the calibration information, is transferred to the receiving board 178 of the controller 176.

In certain embodiments, the calibration system 174 uses a calibration algorithm, as discussed herein, to calibrate the magnetoresistive sensor 120 to account for variations in temperatures, magnetic fields, or other factors that affect the sensor output during sensor operation (i.e., device navigation). The calibration system 174 may be performed continuously or periodically to address the factors noted above. In particular, the calibration coil 122 may be capable of generating a known magnetic field that can be sensed by the sensing components and used to derive, and update continuously, a calibration constant ($\Gamma$) that can be used to correct or otherwise adjust the measured position and orientation information derived using the transmission coils. For example, in one embodiment, the calibration process involves continuously calculating the calibration constant so that it may be used to continuously calibrate the sensor during navigation of the device.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A position and orientation system as utilized in navigation of a surgical or interventional device through vasculature of a patient's body, the system comprising:
   a magneto resistance sensor comprising
   a sensor array that measures magnetic fields; and
   a metallic coil positioned within the magneto resistance sensor at a fixed distance from the sensor array;
   a controller configured to at least read out data from the sensor array;
   a processor having processing circuitry coupled to the controller, wherein the processing circuitry calculate and update a transformation constant of a set of transmitter coils that calibrates the sensor array during calibration and tracking of the surgical or interventional device; wherein the sensor array detects an external magnetic field and uses the transformation constant to generate position and orientation of the surgical or interventional device during the calibration and tracking; and
   wherein the transformation constant is updated to compensate for variations in a plurality of factors.

2. The position and orientation system of claim 1, wherein the position and orientation is used to navigate the surgical or interventional device through vasculature of a patient's body.

3. The position and orientation system of claim 1, wherein the sensor array is a one-axis sensor array, a two-axis sensor array, or a three-axis sensor array.

4. The position and orientation system of claim 1, wherein the magnetoresistance sensor is configured to measure the magnetic field by generating a voltage in response to magnetic fields.

5. The position and orientation system of claim 1, wherein the metallic coil is a calibration coil.

6. The position and orientation system of claim 1, wherein the metallic coil has a B/I value that does not change due to environmental changes, wherein the B/I value is a relationship between magnetic field B and current I.

7. The position and orientation system of claim 1, wherein the processing circuitry further processes the data read out from the sensor array in response to a calibration magnetic field to calculate the transformation constant.

8. The position and orientation system of claim 7, wherein the transformation constant is normalized against a calibration constant with a calibration algorithm.

9. A method, comprising:
driving a transmitter coil to generate a navigational electromagnetic field;
measuring a calibration electromagnetic field generated by a calibration coil at a calibration frequency not in use by the transmitter coil by detecting the calibration electromagnetic field with a sensor array on an electromagnetic sensor;
calculating and updating a transformation constant of the transmitter coil using processing circuitry to create an updated transformation constant as based on the measured calibration electromagnetic field during calibration and tracking of a surgical or interventional device;
calibrating the electromagnetic sensor at one or more transmitter frequencies based on the updated transformation constant;
measuring the navigational electromagnetic field using the calibrated sensor array on the calibrated electromagnetic sensor;
generating position and orientation data of the surgical or interventional device based on the measured navigational electromagnetic field and the updated transformation constant;
wherein the electromagnetic sensor is continuously calibrated during navigation; and
wherein the transformation constant is updated to compensate for variations in a plurality of factors.

10. The method of claim 9, wherein the position and orientation data is used to navigate the surgical or interventional device.

11. The method of claim 9, wherein the sensor array is a one-axis sensor array, a two-axis sensor array, or a three-axis sensor array.

12. The method of claim 9, wherein the magetoresistance sensor is configured to measure the magnetic field by generating a voltage in response to the navigational electromagnetic field and the calibration electromagnetic field.

13. The method of claim 9, wherein the calibration coil has a B/I value that does not change due to environmental changes, wherein the B/I value is a relationship between magnetic field B and current I.

14. The method of claim 9, wherein the processing circuitry further calculates the transformation constant, wherein the transformation constant is normalized against a calibration constant with a calibration algorithm.

15. The method of claim 9, wherein the calibration frequency is different than the one or more transmitter frequencies.

16. One or more tangible, non-transitory, machine-readable media collectively storing instructions executable by a processor to:
drive a transmitter coil to generate a navigational electromagnetic field;
measure a calibration electromagnetic field generated by a calibration coil at a calibration frequency not in use by the transmitter coil by detecting the calibration electromagnetic field with a sensor array on an electromagnetic sensor;
calculate and update a transformation constant of the transmitter coil based on the measured calibration electromagnetic field using processing circuitry to produce an updated transformation constant;
calibrate the electromagnetic sensor at one or more transmitter frequencies based on a calibration constant;
measure the navigational electromagnetic field using the calibrated sensor array on the calibrated electromagnetic sensor;
generate position and orientation data of a surgical or interventional device based on the measured navigational electromagnetic field and the updated transformation constant;
wherein the position and orientation of the surgical or interventional device changes during navigation and the transformation constant is continuously updated so that the electromagnetic sensor can be continuously calibrated; and
wherein the transformation constant is updated to compensate for variations in a plurality of factors.

17. The one or more tangible, non-transitory, machine-readable media of claim 16, wherein the position and orientation data is used to navigate the surgical or interventional device.

18. The one or more tangible, non-transitory, machine-readable media of claim 16, wherein the calibration coil has a B/I value that that does not change due to environmental changes, wherein the B/I value is a relationship between magnetic field B and current I.

19. The one or more tangible, non-transitory, machine-readable media of claim 16, wherein the sensor array is a one-axis sensor array, a two-axis sensor array, or a three-axis sensor array.

* * * * *